(12) United States Patent
Schultz

(10) Patent No.: US 9,149,472 B2
(45) Date of Patent: *Oct. 6, 2015

(54) CONTROLLED RELEASE COMPOSITIONS FOR TREATMENT OF COGNITIVE, EMOTIONAL AND MENTAL AILMENTS AND DISORDERS

(71) Applicant: Jack William Schultz, Alpharetta, GA (US)

(72) Inventor: Jack William Schultz, Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/071,610

(22) Filed: Nov. 4, 2013

(65) Prior Publication Data
US 2014/0065231 A1 Mar. 6, 2014

Related U.S. Application Data

(63) Continuation-in-part of application No. 11/213,018, filed on Aug. 26, 2005, now Pat. No. 8,575,194.

(60) Provisional application No. 60/606,003, filed on Aug. 31, 2004.

(51) Int. Cl.
| A61K 31/47 | (2006.01) |
| A61K 9/50 | (2006.01) |
| A61K 45/06 | (2006.01) |
| A61K 31/198 | (2006.01) |
| A61K 31/4178 | (2006.01) |
| A61K 31/519 | (2006.01) |
| A61K 31/525 | (2006.01) |

(52) U.S. Cl.
CPC . *A61K 31/47* (2013.01); *A61K 9/50* (2013.01); *A61K 31/198* (2013.01); *A61K 31/4178* (2013.01); *A61K 31/519* (2013.01); *A61K 31/525* (2013.01); *A61K 45/06* (2013.01)

(58) Field of Classification Search
CPC ............................................. A61K 31/47
See application file for complete search history.

(56) References Cited

U.S. PATENT DOCUMENTS

| 5,391,555 A | 2/1995 | Marshall et al. |
| 5,629,337 A | 5/1997 | Gray |
| 6,228,398 B1 | 5/2001 | Devane et al. |
| 6,248,308 B1 | 6/2001 | Rubin |
| 6,423,721 B1 | 7/2002 | Harris et al. |
| 6,440,994 B1 | 8/2002 | Sanders, Jr. |
| 6,576,636 B2 | 6/2003 | Webb et al. |
| 6,696,466 B1 | 2/2004 | Dunaway |
| 6,762,193 B1 | 7/2004 | Sanders, Jr. |
| 8,575,194 B1 | 11/2013 | Schultz |
| 2002/0137785 A1 | 9/2002 | Kindness et al. |
| 2004/0219213 A1* | 11/2004 | Burnside et al. ............ 424/473 |
| 2005/0107426 A1* | 5/2005 | Overeem et al. ............ 514/311 |
| 2006/0134217 A1* | 6/2006 | Sandhu et al. ............... 424/472 |
| 2007/0026108 A1* | 2/2007 | Foulger ......................... 426/72 |
| 2007/0154546 A1* | 7/2007 | Zhang et al. ................. 424/468 |

FOREIGN PATENT DOCUMENTS

| WO | 03101434 | 12/2003 |
| WO | 2006066780 | 6/2006 |
| WO | 2007012075 | 1/2007 |
| WO | 2009036287 | 3/2009 |
| WO | 2010041277 | 4/2010 |
| WO | 2011038070 | 3/2011 |
| WO | 2011049706 | 4/2011 |

OTHER PUBLICATIONS

Philip G, Malmstrom K, Hampel FC, Weinstein SF, LaForce CF, Ratner PH, Malice MP, Reiss TF. Montelukast for treating seasonal allergic rhinitis: a randomized, double-blind, placebo-controlled trial performed in the spring. Clin Exp Allergy. Jul. 2002:32(7):1020-8.*
Margaret's Natural Health Blog. http://naturalcowgirl.wordpress.com/2012/03/19/n-acetyl-cysteine-nac-for-those-of-you-who-wonder-what-this-is/, Mar. 2012.*
Science Daily, "Folic Acid May Help Treat Allergies, Asthma", http://www.sciencedaily.com/releases/2009/04/090430065452.htm, 2009.*
Schultz, Jack William; Restriction Requirement for U.S. Appl. No. 14/057,167, filed Oct. 18, 2013, mailed Nov. 22, 2013; 9 pgs.
Schultz, Jack William; Notice of Allowance for U.S. Appl. No. 11/213,018, filed Aug. 26, 2005, mailed Jun. 3, 2013, 10 pgs.
Schultz, Jack William; U.S. Patent Application entitled: Treatment Methods of Cognitive, Emotional and Mental Ailments and Disorders having U.S. Appl. No. 11/213,018, filed Aug. 26, 2005, 16 pgs.
Schultz, Jack William; Restriction Requirement for U.S. Appl. No. 11/213,018, filed Aug. 26, 2005, mailed May 15, 2008, 7 pgs.
Schultz, Jack William; Non-Final Office Action for U.S. Appl. No. 11/213,018, filed Aug. 26, 2005, mailed Aug. 25, 2008, 47 pgs.
Craig, TJ, et al; "The Correlation between allergic rhinitis and sleep disturbance," Journal of Allergy and Clinical Immunology, Nov. 2004, 114(5 Suppl), S139-S145.
Lieberman, HR, "The effects of ginseng, ephedrine, and caffeine on cognitive performance, mood and energy," Nutrition Reviews, Apr. 2001, 59(4), 91-102.
Philip, G, et al.; "Montelukast for treating seasonal allergic rhinitis: a randomized, double-blind, placebo-controlled trial performed in the spring," Clinical and Experimental Allergy, Jul. 2002, 32(7), 1020-1028.
Schultz, Jack William; Final Office Action for U.S. Appl. No. 11/213,018, filed Aug. 26, 2005, mailed Apr. 17, 2009, 28 pgs.
American Heritage Dictionary of the English Language, Boston, MA, Houghton Mifflin, 2007, 1 pg.
Drugs.com. Montelukast, accessed on Apr. 11, 2009, http://www.drugs.com/ppa/montelukast-sodium.html, 6 pgs.
Drugs.com, Zafirlukast, accessed on Apr. 13, 2009, http://www.drugs.com/mtm/zafirlukast.html, 4 pgs.

(Continued)

*Primary Examiner* — Paul Zarek
(74) *Attorney, Agent, or Firm* — Taylor English Duma LLP

(57) ABSTRACT

A montelukast composition having a therapeutically effective amount of montelukast in a sustained release is disclosed. A montelukast composition having a therapeutically effective amount of montelukast in an immediate release and sustained release is also disclosed.

18 Claims, No Drawings

(56) References Cited

OTHER PUBLICATIONS

Bloomberg, Michael; "Leukotriene Modifiers", New York City Asthma Initiative; New York City Department of Health and Mental Hygiene; Mar. 2004, 1 pg.
Schultz, Jack William; Non-Final Office Action for U.S. Appl. No. 11/213,018, filed Aug. 26, 2005, mailed Jan. 6, 2010, 22 pgs.
Altman, LC; "A placebo-controlled, dose-ranging study of montelukast, a cysteinyl leukotriene antagonist. Montelukast Asthma Study Group," Journal of Allergy and Clinical Immunology, Jul. 1998, 102(1), 50-56.
Blaiss MS, "Cognitive, social, and economic costs of allergic rhinitis", Allergy and Asthma Proceedings, Jan. 2, 2000, 21(1), 7-13.
Schultz, Jack William; Final Office Action for U.S. Appl. No. 11/213,018, filed Aug. 26, 2005, mailed Jul. 6, 2010, 6 pgs.
Schultz, Jack William; Non-Final Office Action for U.S. Appl. No. 11/213,018, filed Aug. 26, 2005, mailed Oct. 18, 2012, 6 pgs.
Schultz, Jack William; Applicant Initiated Interview Summary for U.S. Appl. No. 11/213,018, filed Aug. 26, 2005, mailed Nov. 15, 2012, 3 pgs.
Schultz, Jack William; Notice of Allowance for U.S. Appl. No. 11/213,018, filed Aug. 26, 2005, mailed Nov. 28, 2012, 8 pgs.
Schultz, Jack William; Notice of Allowance for U.S. Appl. No. 11/213,018, filed Aug. 26, 2005, mailed Feb. 22, 2013, 8 pgs.
Merck & CO, Inc; "Singulair (Montelukast Sodium)—Tablets, Chewable Tablets, and Oral Granules", Copyright 1998-2007, 18 pgs.
Schultz, Jack William; Issue Notification for U.S. Appl. No. 11/213,018, filed Aug. 26, 2005, mailed Oct. 16, 2013, 1 pg.
Schultz, Jack William; U.S. Patent Application entitled: Treatment Methods of Cognitive, Emotional and Mental Ailments and Disorders, having U.S. Appl. No. 14/057,167, filed Oct. 18, 2013, 16 pgs.
Schultz, Jack William; PCT Application entitled: Controlled Release Compositions for Treatment of Cognitive, Emotional and Mental Ailments and Disorders having U.S. Appl. No. PCT/US13/68356, filed Nov. 4, 2013, 28 pgs.
Schultz, Jack William; International Search Report and Written Opinion for serial No. PCT/US13/68356, filed Nov. 4, 2013, mailed Feb. 28, 2014, 8 pgs.
Schultz, Jack William; Non-Final Office Action for U.S. Appl. No. 14/057,167, filed Oct. 18, 2013, mailed Feb. 21, 2014; 13 pgs.

* cited by examiner

CONTROLLED RELEASE COMPOSITIONS FOR TREATMENT OF COGNITIVE, EMOTIONAL AND MENTAL AILMENTS AND DISORDERS

CROSS-REFERENCE TO RELATED APPLICATIONS

This application is a continuation-in-part of U.S. patent application Ser. No. 14/057,167, filed Oct. 18, 2013, which claims priority to U.S. patent application Ser. No. 11/213,018, filed Aug. 26, 2005, which claims priority to U.S. Provisional Patent Application Ser. No. 60/606,003, filed Aug. 31, 2004, the entire disclosure of each of which is incorporated by reference herein.

FIELD

The present disclosure relates generally to the field of pharmaceutical compositions, more particularly to extended release and controlled dosage forms of montelukast. The present disclosure also includes methods of making extended release and controlled dosage forms of montelukast. The present disclosure also includes the treatment of ailments, and more particularly to a method for treatment of cognitive, emotional and mental ailments.

BACKGROUND

As the aging population increases, the treatment of ailments including the treatment of cognitive, emotional and mental ailments, including memory loss, will become more and more important. Compositions and methods for treating such conditions will be needed. The present disclosure addresses that need.

SUMMARY

A montelukast composition having a therapeutically effective amount of montelukast in a sustained release is disclosed. A montelukast composition having a therapeutically effective amount of montelukast in an immediate release and sustained release form is further disclosed.

DETAILED DESCRIPTION

The present disclosure will now be described more fully hereinafter with reference to the accompanying data, in which some, but not all embodiments of the disclosure are shown. Indeed this disclosure may be embodied in many different forms and should not be construed as limited to the embodiments set forth hereinafter; rather, these embodiments are provided so that this disclosure will satisfy applicable legal requirements.

In general, the disclosure features compositions and methods for the treatment of cognitive, emotional and mental ailments using therapeutically effective amounts of compositions including leukotriene receptor antagonists, leukotriene synthesis inhibitors or leukotriene modifiers, zafirlukasts, montelukasts, other members of the family-lukasts, and zileutons. The present disclosure also includes the aforementioned compositions within rate release modifiers that provide extended release and controlled release profiles.

Compositions comprising montelukast sodium are described herein that provide extended release and controlled release profiles that will improve patients' compliance and improve the patients' conditions overall.

The present disclosure also relates to a novel compressed tablet which is made of two portions (a bi-layer tablet): a portion which comprises a modified release formulation of the montelukast composition and a portion which is an immediate release formulation of montelukast. The present disclosure also relates to novel dosage forms that include immediate and extended release beads of montelukast. The present disclosure also describes methods of making the compositions disclosed herein.

The present disclosure also describes a method, including administering to a patient suffering from a family of mental, emotional and cognitive ailments a therapeutically effective amount of a composition affecting the ailment for a specified period of time for relief of the ailments. The present disclosure may also be used for treating memory loss, lack of attention, poor mood, apathy, and poor cognitive function.

In one implementation, the composition is a leukotriene receptor antagonist.

In another implementation, the composition is a leukotriene modifier.

In another implementation, the composition is a montelukast.

In another implementation, the composition is a zafirlukast.

In another implementation, the composition is a zileuton.

In yet another implementation, the composition is a member of the family-lukast.

In still another implementation, the composition is administered at an initial dosage of about 20-30 mg.

In another implementation, additional dosages are administered at periodic intervals.

In another implementation, the additional dosage is about 5 mg.

In another implementation, the additional dosage is about 10 mg.

In another implementation, the additional dosage is about 20 mg.

In another implementation, the periodic interval is about every 2 hours.

In another implementation, the periodic interval is about every 4 hours.

In another implementation, the maximum daily dosage is about 40 mg.

In another implementation, the maximum daily dosage is about 80 mg.

In another implementation, the ailments result from mild permanent cognitive and short term memory loss.

In another implementation, the ailments are caused by prolonged exposure to levels of mold and fungi.

In another implementation, the mold is *Stachybotrus*.

In another implementation, the ailments can be related to prolonged allergies.

One advantage of the disclosure is that the compositions used in the treatment methods have little to no significant side effects.

Another advantage of the disclosure is that prolonged marked improvement of several cognitive, mental and emotional ailments is realized.

Other objects, advantages and capabilities of the disclosure will become apparent from the following description taken in conjunction with the accompanying data illustrating some embodiments of the disclosure.

At an increasing rate, people are suffering from a series of mental, emotional and cognitive disorders and ailments from a variety of sources. In particular, with the inevitable aging of the Baby Boomer generation, a large number of people are experiencing these disorders and ailments. This particular generation is interested in keeping mental, emotional and cognitive focus with fewer solutions to these ailments and disorders. However, there is increasing discontent as to remedies available to address these ailments and disorders.

In general, the methods described herein are implemented for the treatment of treatment of ailments such as cognitive, emotional and mental disorders. In a specific embodiment, pharmaceutically acceptable doses of leukotriene receptor antagonists, leukotriene synthesis inhibitors or leukotriene modifiers are used to reduce or eliminate several classes of cognitive, emotional and mental disorders. It is understood that these classes spread across a wide spectrum of disorders including, but not limited to memory loss, which can include simple short term or long term memory loss, senility, Alzheimer's, vascular dementia and other types of memory loss and dementia; apathy; depression, fatigue; cognitive losses; loss of focus; loss of libido; loss of the ability to multi-task; loss of sense of humor; repetitive daydreaming; attention deficit disorders and the like.

The leukotriene receptor antagonists, leukotriene synthesis inhibitors or leukotriene modifiers can include a large class of compositions including but not limited to zafirlukasts, montelukasts, other members of the family-lukasts, zileutons.

In a specific embodiment, the method can be used for the treatment of loss of cognitive, mental and emotional ability due to permanent cognitive and mental damage. Such damage can be caused by several reasons including the prolonged exposure to toxic levels of mold that can include *Stachybotrus* molds and other fungi. Such exposure to the molds can be accompanied by strong allergic reactions that can typically cease when the person leaves the physical location of the molds. However, it has been determined that the prolonged exposure to the molds can cause mild permanent cognitive and short term memory loss and other conditions that can result in the cognitive, mental and emotional ailments as described above and further in the example below.

By obtaining treatment using certain classes of compositions, those experiencing the ailments from mild permanent cognitive and short term memory loss and other cognitive, mental and emotional conditions can obtain significant relief. In one implementation, the person suffering from the ailments can take an increased dosage of the compositions, typically 2-3 times the dosage of the same medication used in the treatment of allergies, as an initial dosage at the beginning of the day and can experience almost immediate relief from the ailments. By taking an additional dosage periodically during the day, the patient can experience relief from the ailments all day. In a specific implementation, the initial increased dosage can be 20-30 milligrams of a montelukast sodium compound such as Singulair®, in which marked improvement is noticed within 30-45 minutes. Additional smaller dosages, such as about 10 mg can be taken at four hour intervals to experience prolonged relief.

There can be several mechanisms which can cause the cognitive, mental and emotional ailments resulting in mild permanent cognitive and short term memory loss and other cognitive, mental and emotional conditions. In additional, it is understood that there are several mechanisms that can cause the relief upon administration of the composition such as, but not limited to the mechanisms associated with leukotriene receptor antagonists, leukotriene synthesis inhibitors/or leukotriene modifiers, as well as simple relief from chronic inflammation that can result in neurological effects.

EXAMPLE

Patient 1

A case study of a patient having a long history of allergies was performed. During his teenage years, the patient had allergies, but enjoyed forty five years of freedom from allergies. Late in 1995, the patient had recurring allergies and additional allergies previously not present. The patient suffered chronic sinusitis and sought the services of an Eye Nose Throat group. Under typical treatment, the conditions did not improve and in 1997 the patient had sinus surgery and rhinoplasty. Shortly thereafter, the symptoms returned and continued through 2003. The patient then began experiencing cognitive, mental and emotional ailments that appeared to have no connection to his chronic allergies. These ailments included short term or long term memory loss, dementia, apathy, depression, fatigue and chronic fatigue, cognitive losses, loss of focus, "foggy days," loss of libido, loss of the ability to multi-task, loss of sense of humor, repetitive daydreaming, loss of the sense of time, and disorientation.

Concurrently in 1999, the patient found that his business location had toxic levels of mold that had been growing in the workplace from 1995 forward. *Stachybotrus* and other fungi had been present during the outset of the allergies in 1995. Through blood tests, the patient was found to have a "hole" in his immune system, and as a result, had a high sensitivity to these and other molds. In general, the patient was ordered in 2000 not to return to the workplace until it was cleaned of dangerous high levels of mold. The recommended course of action of leaving the source of the mold typically results in patients marked improvement in the allergic condition. However, the patient discovered that the cognitive, mental and emotional ailments persisted. His general health deteriorated to a point where he could wake up and not be aware of his own name until after several hours of being awake. For a period of five months the patient could wake up, remember his name after a few hours, and if prompted by a reminder from a family member, could perform daily tasks. Even with reminders, the patient experienced apathy that resulted in the tasks being ignored.

The patient was able to seek the help of mold experts in 2001 who recommended staying away from mold, but diagnosed the patient with mild permanent cognitive and short term memory loss that were apparently the devastating results of being exposed to the mold. The patient was used to being a business man who had the great ability to multitask and run several successful businesses. The patient now found himself struggling to meet the basic needs of everyday living. With great effort, the patient could focus to complete simple tasks.

The patient was still experiencing allergies, so in an unrelated trip to an allergy physician, the patient was prescribed the medication Singulair®. The patient discovered that when he took the medication, he experienced cognitive improvement. A typical dosage of the Singulair® is about 10 mg. On a trial basis, the patient took approximately 2-3 times the dosage or about 20-30 mg and found marked cognitive, mental and emotional improvement. The patient also experienced a marked decrease in apathy and an increase in sense of humor. Upon waking, the patient takes the higher dosage of Singulair® and experiences relief from the diagnosed mild permanent cognitive and short term memory loss in about 30-45 minutes. Furthermore, taking an additional 10 mg dose every four hours continues the relief from the diagnosed mild permanent cognitive and short term memory loss, which includes the other symptoms the patient was experiencing. When the patient ceases the dosage, the symptoms typically return in a 24 hour period.

In one embodiment, as described in the example, montelukast sodium can be implemented to treat the ailments and disorders as described. A 10 mg tablet can be taken orally upon awakening. Typically, in about 45 minutes to one hour, a patient can experience relief from the ailments and disorder and begin to have better mental focus on daily routines. In a typical implementation, the patient can take another 10 mg dose in about two hours after the initial dose. Booster dosages of about 5 mg, typically in a chewable tablet, can be taken to have heightened focus throughout the day. Similar booster dosages can be taken at 3-4 hour intervals throughout the day. In another implementation, an additional 10 mg dose can be taken after the second 5 mg dose if such advantageous effects wear off. Additional 10 mg doses can be taken to achieve higher effects of focus. In another implementation, booster dosages of 5 mg can be taken at intervals of about every 2 hours in order to achieve very high levels of focus. It has been determined that such mega-dosing can result in very talkative mental states and highly sensitive mental alertness. In the example discussed above, a maximum dose of 40 mg in one day has been taken. The Singulair® product typically recommends 10 mg per day.

In another embodiment, a zafirlukast product such as Accolate® and Vanticon® can be implemented. In one implementation, a 20 mg oral dose can be taken upon awakening followed by a 10 mg dose after 2 hours and a 10 mg repeated dose in 4 hours and a final dose of 20 mg another 4 hours later. Accolate® provides heightened focus but results in a less "wired" disposition. The highest dosage taken by the patient in the example above has been 80 mg in a daily dosage. The Accolate® recommended dosage is 20 mg in the morning and evening.

In other embodiments, other leukotriene modifiers can be implemented including but not limited to Zylow® (zileuton), Onon® (pranlukast), Aziaire® (pranlukast) and Xolair® (omalizumab).

In methods of administering the compositions described herein can also be implemented to treat other disorders including but not limited to restless leg disorder and the like.

EXAMPLE

Patient 2

A 65 year old white male was diagnosed with mild symptoms of forgetfulness.

The patient was administered 20 mg of montelukast sodium upon rising in the morning. The patient took an additional 10-20 mg after about every 2 hours during waking hours. The patient did not know the identity of the composition.

The patient noted improvement in symptoms within 24 hours of onset of medication use.

The patient took the montelukast for over a week and then stopped.

The symptoms recurred within 24 hours of discontinuation.

Then, two weeks later, the patient began to take 20 mg of montelukast sodium and an additional 10-20 mg after about every 2 hours during waking hours. The patient complied with this prescription for five days and experienced marked improvement in symptoms while sticking to the regimen. After the patient stopped taking montelukast sodium, the symptoms returned again.

The patient stated he would like to try the regimen longer, but the patient found it hard to take the composition every two hours.

No side effects reported.

EXAMPLE

Patient 3

A 69 year old white female had symptoms of cognitive ailments including complaining of feeling like she was in a fog frequently; mild memory problems, and the patient found it hard to focus on tasks.

The patient was administered 10 mg of montelukast sodium upon rising in the morning. The patient took an additional 10 mg after about every 2 hours during waking hours. The patient did not know the identity of the composition.

The patient noted significant improvement in symptoms while on medication.

After the patient complied with the aforementioned prescription for five days, the patient decreased the dosage to only one 10 mg montelukast sodium daily, in the morning. The patient still noted mild improvement in focus and concentration at the once daily dose.

No side effects noted.

EXAMPLE

Patient 4

A 52 year old white female with symptoms of decreased concentration and focus along with memory recall and forgetfulness issues. The patient was also diagnosed with depression and anxiety.

The patient was administered 10 mg of montelukast sodium upon rising in the morning along with an antidepressant. The patient took an additional 10 mg after about every 2 hours during waking hours. The patient did not know the identity of the composition. The patient noted significant improvement in symptoms.

EXAMPLE

Patient 5

A 56 year old white female had symptoms of forgetfulness and problems with word recall.

A patient was administered 10 mg of montelukast sodium upon rising in the morning. The patient took an additional 10 mg after about every 2 hours during waking hours. The patient did not know the identity of the composition.

The patient complained that 6 doses daily caused difficulty sleeping. After reducing the schedule to five doses daily, the problem was resolved.

The patient noted significant improvement in memory and recall issues within 24 hours of initiation of the prescribed protocol. The patient followed the aforementioned dosage schedule for five days.

No other side effects noted.

The patient expressed a desire to continue the prescribed medication long term, but the patient did not like taking the composition every two hours.

After taking the aforementioned montelukast dosage schedule for five days, the patient discontinued the protocol and symptoms recurred within 24-48 hours.

EXAMPLE

Patient 6

A 69 year old white male had symptoms of cognitive ailments including complaining of feeling like he was frequently in a fog; mild memory problems, and the patient found it hard to focus on tasks.

The patient was administered 80 mg of montelukast sodium once, upon rising in the morning. The patient noted improved mental clarity in the morning and better mood throughout the day.

The patient was administered 50 mg of montelukast sodium once, upon rising in the morning. The patient noted improved mental clarity in the morning and better mood throughout the day.

Montelukast sodium has been found to alleviate and treat memory loss, forgetfulness, apathy, emotional and cognitive ailments, and depression. Montelukast has also been found to improve cognitive function including focus, memory, recall, and concentration. In most cases, treatment of these ailments requires multiple dosages of 5 mg to 20 mg over the course of the day. While one large dosage does improve mood overall, the benefits of improved memory and cognitive function are better realized through controlled release throughout the day. However, patient compliance tends to decrease when more than one dosage is required.

To improve patient compliance, the present disclosure also includes compositions that provide montelukast on controlled release dosages that provides extended release and a continual release profile of montelukast. While immediate release dosages larger than 30 mg report improved mood, it was found that sustained release montelukast was necessary to improve memory and improve cognitive function throughout the day.

Montelukast sodium is the active pharmaceutical ingredient of SINGULAIR®, and is approved for the treatment of asthma and allergic rhinitis. The molecular structure of montelukast is as shown below:

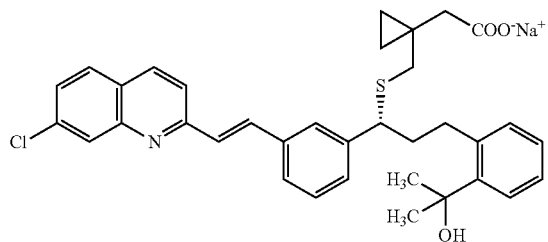

Montelukast sodium is described in U.S. Pat. No. 5,565,473 which is incorporated by reference herein. While montelukast is most commonly in the form of a sodium salt, other salts are known and may be used for the compositions of this disclosure.

Montelukast is a leukotriene antagonist and is currently approved for the treatment of asthma and allergic rhinitis. The dosages used to treat asthma and allergic rhinitis are typically 10 mg or less. It is also understood that larger dosages provide no additional benefit in treating asthma and allergic rhinitis. Dosages of montelukast larger than 20 mg are not typically available. Additionally, controlled release dosages provide no additional benefit in treating asthma and allergic rhinitis. Controlled release dosages of montelukast sodium of any amount, especially larger than 20 mg, are not known in the prior art. The current state of the art teaches that neither of these elements are needed in the montelukast compositions of the prior art.

For convenience, the total daily dosage may be divided and administered in portions during the day if desired or at one time, morning, afternoon, night as well as biphasic, triphasic, etc. Controlled, delayed (e.g. enteric), and sustained release formulations are within the scope of this disclosure and, for convenience, are termed "controlled release" formulations.

The montelukast compositions disclosed herein provide an improved release profile for montelukast, since it provides a rapid increase in montelukast levels in blood and maintains a beneficial level of montelukast in the blood for an extended period of time.

Many different embodiments of montelukast compositions disclosed herein that provide a controlled release of montelukast. Controlled release dosage forms of montelukast may be montelukast encapsulated in or mixed with a release rate modifying matrix.

Other embodiments of the disclosure include those wherein: (1) the solid dosage form is a tablet coated with one or more coats at least one of which optionally comprises a flavorant; (2) vitamins and minerals are mixed with the one or more excipients prior to pressing into a tablet.

Administration of known montelukast forms generally results in reductions of blood montelukast levels between consecutive doses. These reductions can be due to the time interval between dosages, which is usually daily. The reductions of montelukast in blood levels is responsible for returning symptoms of cognitive impairment, memory loss, and mental fog.

The montelukast compositions described herein may also comprise essential vitamins and minerals that are necessary for improved cognitive function. For example, vitamin $B_9$ as folate, including reduced folates, N-acetyl-L-cysteine, vitamin $B_{12}$ as cobalamin, vitamin $B_6$ as pyridoxal phosphate, and vitamin $B_2$ as riboflavin. Some essential minerals include zinc and magnesium.

Additionally, the montelukast compositions described herein may also comprise or be administered with Alzheimer's drugs.

In one aspect, the controlled release dosage form of montelukast described herein is a controlled release montelukast solid dosage form comprising one rapidly dissolving montelukast and a slowly dissolving form of montelukast and at least one pharmaceutically acceptable carrier, wherein the solid dosage provides a controlled release of the montelukast.

Pharmaceutically acceptable excipients which can be included in the montelukast composition include, for example, tablet binders, acidifying agents, alkalinizing agents, adsorbents, preservatives, antioxidants, buffering agents, colorants, dispersants, thickeners, solubilizing agents, encapsulating agents, stiffening agents, tablet antiadherents, tablet and capsule diluents, tablet coating agents, tablet direct compression excipients, tablet disintegrants, tablet glidants, tablet lubricants, tablet opaquants, and tablet polishing agents.

In one form, the active ingredients of the montelukast composition are mixed with the one or more excipients and compressed to form a tablet. The tablet is then optionally coated with one or more coats, one of which may comprises a flavorant.

This disclosure includes many different ingredients that could be defined as an "active" ingredient depending on the particular embodiment. All embodiments will include the active ingredient of montelukast. Other embodiments may include essential vitamins and minerals that are necessary for improved cognitive function. For example, vitamin $B_9$ as folate, including reduced folates, N-acetyl-L-cysteine, vitamin $B_{12}$ as cobalamin, vitamin $B_6$ as pyridoxal phosphate, and vitamin $B_2$ as riboflavin. Some essential minerals include zinc and magnesium.

The compositions described herein can be made and used in a wide variety of forms, and may be a solid dosage form. The solid dosage form may be a capsule or compressed tablet. When a tablet form is used, the tablet may be coated (e.g., film-coated). The capsule is generally made by mixing the active ingredients (which can be powdered, granulated, coated, agglomerated, or some combination of these) with one or more excipients to form a mixture which is subsequently loaded into the capsule. The capsule may be a hard gelatin capsule. The capsule halves are then joined.

The montelukast composition may be a pressed solid dosage form including a tablet, capsule, chewable tablet, lozenge, granule or pellet. The dosage form may be provided as a single or subdivided into several unit doses containing appropriate quantities of the vitamins.

The components of the solid dosage form may be finely divided, i.e., powdered or granulated so as to provide a uniform distribution of ingredients throughout the dosage form.

The montelukast and the vitamins that have been coated, granulated, or agglomerated individually or in combination can be further coated, agglomerated or granulated prior to being compressed into a solid dosage form.

The montelukast composition of the disclosure will be able to provide a controlled delivery of montelukast to a mammal for a period of not less than 3 hours up to about 48 hours, or in another embodiment, not less than 8 hours up to about 15 hours.

In one embodiment of the present disclosure, a sustained release formulation comprises montelukast mixed with a polymer blend which consists of at least one hydrophilic polymer and at least one water-insoluble polymer. In a further embodiment, the sustained release formulation may comprise a combination of montelukast and at least one other drug including, but not limited to, a vitamin such as vitamin $B_9$ or folate as L-methylfolate, vitamin B 12, N-acetyl-L-cysteine, vitamin $B_2$, or vitamin $B_6$, or an Alzheimer's drug such as donepezil hydrochloride, or a mineral such as magnesium, copper, or zinc, or a combination thereof.

The sustained release formulation may comprise montelukast in the amount of from 20 mg to 100 mg. Dosages may depend on the severity of the ailments, weight, and age of the patient. One embodiment includes montelukast in the amount of from 60 mg to 80 mg.

Hydrophilic polymers suitable for use in the sustained release formulation include: one or more natural or partially or totally synthetic hydrophilic gums such as acacia, gum tragacanth, locust bean gum, guar gum, or karaya gum, modified cellulosic substances such as methylecllulose, hydroxomethylcellulose, hydroxypropyl methylccllulose, hydroxypropyl cellulose, hydroxyethylcellulose, carboxyinethylcellulose; proteinaceous substances such as agar, pectin, carrageen, and alginates; and other hydrophilic polymers such as carboxypolymethylene, gelatin, casein, zein, bentonite, magnesium aluminum silicate, polysaccharides, modified starch derivatives, and other hydrophilic polymers known to those of skill in the art or a combination of such polymers.

These hydrophilic polymers gel and dissolve slowly in aqueous acidic media thereby allowing the montelukast to diffuse from the gel in the stomach. When the gel reaches the intestines, it dissolves in controlled quantities in the higher pH medium, where the montelukast itself is fairly absorbable to allow sustained release of montelukast throughout the digestive tract.

Water-insoluble polymers which are suitable for use in the sustained release formulation are polymers which generally do not dissolve in solutions of a pH below 5 and dissolve more slowly in basic solutions than the hydrophilic polymer. Because the polymer is insoluble in low pH environments such as those found in gastric fluid, it aids in retarding drug release in those regions. Likewise, because the polymer dissolves more slowly in solutions of higher pH than hydrophilic polymers, it aids in retarding drug release throughout the intestines. This overall delayed release results in a more uniform serum concentration of montelukast.

Some water-insoluble polymers suitable for use in this disclosure include: polyacrylic acids, acrylic resins, acrylic latex dispersions, cellulose acetate phthalate, polyvinyl acetate phthalate, hydroxypropyl methylcellulose phthalate and other polymers common to those of skill in the art.

A sustained release formulation of the present disclosure may further comprise pharmaceutical additives including, but not limited to: lubricants such as magnesium stearate, calcium stearate, zinc stearate, powdered stearic acid, hydrogenated vegetable oils, talc, polyethylene glycol, and mineral oil; colorants such as Emerald Green Lake and various FD&C colors; binders such as sucrose, lactose, gelatin, starch paste, acacia, tragacanth, povidone polyethylene glycol, Pullulan and corn syrup; glidants such as colloidal silicon dioxide and talc; surface active agents such as sodium lauryl sulfate, dioctyl sodium sulfosuccinate, tricthanolamine, polyoxyetiylene sorbitan, poloxalkol, and quarternary ammonium salts; preservatives and stabilizers; excipients such as lactose, mannitol, glucose, fructose, xylose, galactose, sucrose, maltose, xylitol, sorbitol, chloride, sulfate and phosphate salts of potassium, sodium, and magnesium; and/or any other pharmaceutical additives known to those of skill in the art. In one embodiment, a sustained release formulation further comprises magnesium stearate and Emerald Green Lake. In another embodiment, a sustained release formulation further comprises magnesium stearate and FD&C Blue #1 Aluminum Lake Dye.

The present sustained release formulation controls the release of montelukast into the digestive tract slowly over time. To maintain a blood concentration of montelukast which provides good therapeutic effect, the release, or dissolution, of montelukast from a formulation matrix is retarded and/or controlled through the intestines. The combination of hydrophilic and water-insoluble polymers of the sustained release formulation of the present disclosure gels when exposed to media of low pH. This creates a matrix out of which montelukast can diffuse. When the gelled polymer combination is exposed to media of a higher pH, the gel begins to slowly dissolve thereby releasing montelukast at a controlled rate.

A sustained release formulation of the present disclosure may be manufactured according to any appropriate method known to those of skill in the art of pharmaceutical manufacture. In one embodiment, montelukast and a hydrophilic polymer may be mixed in a mixer with an aliquot of water to form a wet granulation. The granulation may be dried to obtain hydrophilic polymer encapsulated granules of montelukast. The resulting granulation may be milled, screened, then blended with various pharmaceutical additives, water insoluble polymer, and additional hydrophilic polymer. The formulation may then tableted and may further be film coated with a protective coating which rapidly dissolves or disperses in gastric juices.

To improve the $C_{max}$ and speed of appearance of montelukast in patients while maintaining therapeutic effect for at least twelve hours, a portion of a sustained release formulation of the present disclosure as described above may be combined with a portion of an immediate release formulation in a bi-layer tablet.

The immediate release formulation may comprise montelukast and various pharmaceutical additives such as lubricants, colorants, binders, glidants, surface active agents, preservatives, stabilizers, as described above and/or any other pharmaceutical additives known to those of skill in the art. In one embodiment, an immediate release formulation comprises montelukast, microcrystalline cellulose, sodium starch glycolate, and magnesium stearate. In another embodiment, an immediate release formulation may comprise about 58% montelukast, about 33% microcrystalline cellulose, about 8% sodium starch glycolate, and about 0.3% magnesium stearate.

The immediate release formulation may comprise montelukast in the amount of from 5 mg to 25 mg. Dosages may depend on the severity of the ailments, weight, and age of the patient.

The bi-layer tablet may be manufactured according to any method known to those of skill in the art. The resulting tablet may comprise the two portions compressed against one another so that the face of each portion is exposed as either the top or bottom of the tablet, or the resulting tablet may comprise the sustained release portion in the center coated by the immediate release portion so that only the immediate release portion is exposed. In one embodiment, a bi-layer tablet of the present disclosure comprises the two portions compressed against one another so that the face of each portion is exposed.

The tablets may be made with any ratio of sustained release to modified release formulation which results in a blood profile demonstrating appropriate therapeutic effect over extended time periods. In one embodiment, the bi-layer tablets comprise portions of sustained release formulation and immediate release formulation which result in about a four-to-one (4:1) ratio of montelukas,t respectively. For example, in an 80 mg bi-layer modified release montelukast tablet of the present disclosure, there may be about 20 mg of montelukast in the immediate release layer and about 60 mg of montelukast in the sustained release layer.

In one embodiment, the two formulations may then be compressed to make bi-layer tablets wherein about 75% of each tablet may be sustained release formulation and about 25% of each tablet may be immediate release formulation. The tablets may be any dosage strength, size, or shape.

The immediate release portion of the bi-layer tablet is formulated to dissolve in aqueous media of low pH, such as that found in the stomach, to quickly release the montelukast contained within the portion. This results in rapid bioavailability of a high concentration of montelukast.

In another embodiment, the disclosure provides a modified release, multi-particulate dosage form of a montelukast comprising one or more bead populations which provides an extended release profile of the montelukast. One of the bead populations is an extended release bead population typically comprising a coating of a water insoluble polymer alone, or in combination with a water soluble polymer, applied onto active containing cores. The active core of the dosage form of the present disclosure may comprise an inert particle such as a sugar sphere, or an acidic or alkaline buffer crystal, which is coated with montelukast. The first coating formulation may contain, in addition to the active, a binder such as hydroxypropyl cellulose. The drug layered beads may be coated with a protective seal coating of OPADRY® Clear to produce immediate release beads. Alternatively, the core particle may be formed by granulating and dry milling and/or by extrusion and spheronization of a pharmaceutical composition containing the active. The amount of drug in the core will depend on the dose required and typically varies from about 5 to about 60% by weight.

Extended release beads can be produced by applying a functional membrane comprising a water insoluble polymer alone or in combination with a water soluble polymer onto immediate release beads. The capsule formulation for once a day, oral administration of a montelukast prepared in accordance with the present disclosure comprises extended release beads containing the montelukast and, optionally, immediate release beads Immediate release beads allow immediate release of the montelukast while extended release beads allow an extended release profile of the active over several hours. Upon oral administration, such a capsule formulation provides for therapeutically effective plasma profiles over an extended period of time, thereby resulting in improved patient compliance.

In accordance with one embodiment of the disclosure a pharmaceutical dosage form of a montelukast is provided. The dosage form includes one or more bead populations and provides a modified release profile. At least one of the bead populations includes extended release beads (ER) wherein the ER beads include a core particle immediate release bead containing a montelukast and an extended release coating comprising a water insoluble polymer surrounding the core. The dosage form, in accordance with certain embodiments, when dissolution tested using United States Pharmacopoeia Apparatus exhibits a drug release profile substantially corresponding to the following pattern:

after 2 hours, no more than about 40% of the total montelukast is released;
after 4 hours, from about 40-65% of the total montelukast is released;
after 8 hours, from about 60-85% of the total montelukast is released; and
after 12 hours, from about 75-85% of the total montelukast is released.

A pharmaceutical composition with extended release beads would typically provide from 30 mg to 100 mg of montelukast.

A pharmaceutical composition with immediate release beads would typically provide from 5 mg to 25 mg of montelukast.

A pharmaceutical composition with both immediate release and extended release beads would typically provide from 5 mg to 25 mg of montelukast in immediate release and 30 mg to 80 mg of montelukast in extended release. Precise dosages will depend on the size of the patient and the severity of the symptoms.

The dosage form thereby provides a therapeutically effective plasma concentration over an extended period of time, typically over a period of at least 12 hours and up to 24 hours for improved memory, mental clarity, mood, attention span, and improved cognitive function.

The montelukast composition can be coated with a pharmaceutically acceptable film forming material which permits release of the montelukast in the gastrointestinal tract of a mammal administered the composition. Suitable coatings include those described below. A coated montelukast composition should provide increased montelukast bioavailability by minimizing interaction between divalent cations, such as calcium, manganese, copper, and magnesium.

In addition, coating can also stabilize a component, particularly where the component which can lose its physiological activity, or have such activity decreased or inhibited, upon exposure (particularly prolonged exposure) to an environmental factor such as light, oxygen, or moisture. Coating of unpleasant-tasting or -smelling components is contemplated when the montelukast composition described herein is a chewable or quickly-dissolving composition. When the montelukast composition is a tablet, coating of individual components is generally not necessary, although coating of the tablet can serve to improve the stability, appearance, taste, odor, or handling characteristics of the tablet.

Various forms of extended release particles or coatings along with immediate release particles or coatings can also be combined in the present formulations to deliver the various montelukast compositions, vitamins and minerals at various rates. For example, certain agents such as thiamine, niacinamide, pyridoxine, folate, and riboflavin could be released over an extended period of time from two hours up to 24 hours while other agents such as vitamin $B_{12}$, copper, zinc, and magnesium, as well as montelukast, can be administered in immediate release forms. Formulations having a combination of particles with different release profiles are well known and are prepared according to procedures and techniques known to the artisan of ordinary skill.

If coated, the pressed solid dosage form of the disclosed compositions comprise a film coating and a compressed solid core. The film coating comprises one or more film forming agents, e.g. combinations of film forming agents are used in some embodiments of the film coating. This combination of film forming agents can provide a formulation having a combined delayed and controlled release of therapeutic agent. The film coating on the dosage form can also comprise a flavorant and/or colorant, such as a pigment or dye. The coating for the pressed tablet may be a rapidly dissolving finish or polish coat comprising a cellulosic polymer, a colorant, a flavorant and a wax.

A process for making a carbohydrate-based agglomerate generally comprises the steps of forming a fluidized bed of carbohydrate particles, intermittently spraying a solution of the water soluble binder in a droplet size of from about 20 micrometers to about 100 micrometers into the fluidized bed so as to cause intimate mixing of solution and carbohydrate particles and adhesion together of carbohydrate particles to form agglomerated particles, drying the particles in the fluidized bed between intermittent sprayings, and continuing spraying and drying until the desired amount of solution has been sprayed into the bed. Thereafter, the agglomerated particles are dried to a desired moisture content or the equilibrium moisture content. The amount of liquid binder solution sprayed corresponds to a binder content in the agglomerate of from about 1 percent to about 10 percent by weight of the agglomerate (excluding active ingredient). The carbohydrate-based agglomerate and the montelukast can be mixed, in a low shear blender, in the following proportion by weight of the finished agglomerate (including active ingredient) agglomerate, about 50 percent to about 90 percent; active ingredient, from about 10 percent to about 50 percent. A lubricant is also mixed together with the agglomerate and the active ingredient in the proportion of from about 0.4 percent to about 1 percent by weight of the finished agglomerate (including active ingredient). Flavors can also be mixed with the agglomerate and the montelukast.

Some agglomerates include those comprising the following materials: dextrose monohydrate; dextrose monohydrate and maltodextrin; fructose; dextrose; mannitol; fructose and maltodextrin; sucrose; sucrose and maltodextrin; lactose; lactose and maltodextrin; maltose; maltose and maltodextrin; xylose; xylose and maltodextrin. Aqueous solutions of the following materials can be used as a liquid binder solution: corn syrup solids; dextrose; sucrose; poly(vinylpyrrolidone); cooked starch paste; and combinations of the foregoing, any of which may also include maltodextrin. In such solutions, the maltodextrin binder material may have a DE (dextrose equivalence) of less than about 20% or in the range of from about 5% to about 12%.

The terms "film forming agent" includes polymeric compounds (of natural, synthetic, semi-synthetic or genetically engineered sources) which will form a film coating around the solid core of the formulation. Some of the film forming agents useful in the disclosure are further described herein.

The film coating employed can comprise a polymer with a pH dependent solubility which would release a major portion of one or more vitamins and/or minerals in the stomach, ileum, jejunum, small intestine or large intestine a person taking the tablet. The thickness of the film coating can be varied as desired.

The vitamins and minerals contained within the montelukast composition are formulated as pharmaceutically acceptable salts when necessary. As used herein, "pharmaceutically acceptable salts" refer to derivatives of the disclosed compounds wherein a compound is modified by making an acid or base salts thereof. Examples of pharmaceutically acceptable salts include, but are not limited to, mineral or organic acid salts of basic residues such as amines; alkali or organic salts of acidic residues such as carboxylic acids; and others known to those of ordinary skill in the art. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and others known to those of ordinary skill in the art; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. The pharmaceutically acceptable salts of these compounds are available from well known commercial sources.

Examples of other binders which can be added to the formulation include, for example, acacia, tragacanth, gelatin, starch, cellulose materials such as methyl cellulose and sodium carboxymethyl cellulose, alginic acids and salts thereof, polyethylene glycol, guar gum, polysaccharide, sugars, invert sugars, poloxomers, collagen, albumin, gelatin, cellulosics in non-aqueous solvents, pre-gelatinized starch, starch paste and combinations of the above. Other binders include, for example, polypropylene glycol, polyoxyethylene-polypropylene copolymer, polyethylene ester, polyethylene glycol, polyethylene sorbitan ester, polyethylene oxide or combinations thereof and others known to those of ordinary skill in the art.

The montelukast compositions may also comprise essential vitamins and minerals that necessary for cognitive function, or may be administered alone, but in combination with an additional nutritional supplement providing additional vitamins and minerals necessary for cognitive health.

Reduced Vitamin $B_9$: The health benefits and even requirements of folic acid are well known. In addition to folic acid, reduced folates are also beneficial for some people's nutrition. Folic acid is the most oxidized state of Vitamin $B_9$. Levomefolic acid, also known as L-methylfolate and 5-methyltetrahydrofolate, is the active form of folic acid used at the cellular level for DNA reproduction, the cysteine cycle and the regulation of homocysteine among other functions. Reduced folates are more bioactive and are more readily available for the cells to use. A combination of montelukast with a reduced folate has a synergistic effect.

Effective amounts of Vitamin $B_9$ range from 100 mcg to 8 mg.

Vitamin $B_{12}$ is essential for appropriate folic acid metabolism. Vitamin $B_{12}$ also plays a role in maintaining cellular integrity of the central nervous system, which is why including Vitamin $B_{12}$ in a drug with montelukast would be beneficial. Vitamin $B_{12}$, may be provided as cyanocobalamin to mitigate any deficiency of this essential vitamin.

Effective amounts of Vitamin $B_{12}$ range from 50 mcg to 1.5 mg.

Vitamin $B_6$ is a water-soluble vitamin and is part of the vitamin B complex group. Vitamin $B_6$ is a cofactor in many reactions of amino acid metabolism, including transamination, deamination, and decarboxylation. The primary role of vitamin $B_6$ is to act as a coenzyme to many other enzymes in the body that are involved predominantly in metabolism. This role is performed by the active form, pyridoxal phosphate. Pyridoxal phosphate-dependent enzymes play a role in the biosynthesis of five important neurotransmitters: serotonin, dopamine, epinephrine, norepinephrine, and gamma-aminobutyric acid (GABA).

Effective amounts of Vitamin $B_6$ range from 100 mg to 10 mg.

Omega-3 fatty acids may be found in marine fats. They have been shown to be important in the prevention of preeclampsia, preterm delivery, and early rupture of the membranes. Enhanced cognitive function and improved visual acuity in babies born to mothers supplemented with docosahexaenoic acid (DHA) have also been noted. There has been a decrease in maternal postpartum depression when supplemented with DHA. Cold water fish are the highest dietary sources of DHA and it is also available in the eggs of chickens supplemented with micro-algae.

Effective amounts of Omega-3 fatty acids range from 100 mg to 800 mg.

N-acetyl-L-cysteine has been shown to interact with various metabolic pathways. Oxidative stress has been shown to play a pivotal role in neuronal dysfunction and death in various neurodegenerative diseases, including sickle cell disease (SCD), myoclonus epilepsy of the Unverricht-Lundborg type, Alzheimer's disease, Parkinson's disease, tardive dyskinesia, and Down's syndrome. Free radical damage from oxidative stress has long been thought to play an important role in age-related neurodegenerative disorders. It has been suggested that free radical damage compromises composition integrity of cell membranes, which decreases membrane fluidity. Oxidative stress can in some cases result in cognitive impairments. Antioxidants have been found to both prevent, treat, and reverse learning and memory deficits induced by free radicals. N-acetyl-L-cysteine is an antioxidant used to combat oxidative stress-induced damage. Studies have shown that N-acetyl-L-cysteine protects against oxidative stress in peripheral tissues and in the central nervous system. Additionally, it has been found to reverse age-related impairments in memory.

The therapeutic use of antioxidants depends also on their ability to cross the cell membrane and those designed as neuroprotective treatment in acute or chronic neurological disorders should readily cross the blood-brain barrier (BBB). N-acetyl-L-cysteine has been shown to cross the BBB and can accumulate in the brain treating and reversing memory impairment. By increasing levels of brain cysteine, N-acetyl-L-cysteine is able to modulate glutamatergic and dopaminergic pathways. Studies have shown that N-acetyl-L-cysteine can influence a reduction in synaptic release of glutamate and an increase in dopamine release.

Effective amounts of N-acetyl-L-cysteine range from 100 mg to 800 mg.

Montelukast is also believed to treat oxidative stress and decrease inflammation in the nervous system.

Additionally, montelukast may be administered to a patient along with an Alzheimer's drug, such as Donepezil. Controlled studies have shown treatment of Alzheimer's patients with Donepezil experience modest benefits in cognition and/or behavior. A combination of montelukast and Donepezil yield synergistic affects.

Controlled release of montelukast can be achieved by different approaches, such as using commercially available control release polymers, montelukast granulated by control release polymers or coating films, bilayer tablets in which different release design in each layer, and tablets containing montelukast coated by control release film.

ILLUSTRATIVE EXAMPLES

There are many polymers commercially available for control release formulation, such as hydroxypropyl methycellulose (HPMC), hydroxylpropylcellulose (HPC), Carbomer Homopolymer Type A and B, as well as Polycarbophil and calcium polycarbophil.

Example for 10-12 hrs of linear release tablets or hardcapsule by Methocel K4, K15, and K100 (HPMC):

Control Release Tablets or Hardcapsules by Polymers

Example A

| | |
|---|---|
| Montelukast | 60 mg |
| Microcrystalline cellulose (MCC) | 100 mg |
| Dibasic calcium phosphate dehydrate | 50 mg |
| Methocel K15 (Methocel K100) | 70 mg (50 mg) |
| Stearic acid | 2.8 mg (2.6 mg for Methocel K100) |

Example B

| | |
|---|---|
| Montelukast | 25 mg |
| Microcrystalline cellulose (MCC) | 90 mg |
| Dibasic calcium phosphate dehydrate | 30 mg |
| Methocel K15 (Methocel K100) | 50 mg (30 mg) |
| Stearic acid | 2 mg (1.8 mg for Methocel K100) |

Combination of Methocel K4, K15 and K100 can be used in the formulation to achieve the designed release profile.

Example for 10-12 hrs of linear release tablets or hardcapsule by Carbomer Homopolymer Type A and B:

Control Release Tablets

Example A

30% Carbopol 71G NF polymer in the tablets or hardcapsule formulation for 10-12 hr of linear release profile

| | |
|---|---|
| Montelukast | 60 mg |
| Microcrystalline cellulose (MCC) | 80 mg |

| | |
|---|---|
| Dibasic calcium phosphate dehydrate | 30 mg |
| Starch | 30 mg |
| Carbopol 71G | 85 mg |
| Stearic acid | 2.8 mg |

Example B

About 5% Carbopol 971P in the tablets formulation for 10-12 hr of linear release profile

| | |
|---|---|
| Montelukast | 60 mg |
| Microcrystalline cellulose (MCC) | 100 mg |
| Dibasic calcium phosphate dehydrate | 30 mg |
| Starch | 30 mg |
| Carbopol 971P | 12 mg |
| Stearic acid | 2.2 mg |

Any commercial available excipients can be used in the formulation.

Montelukast tablets coated by control release film such as Kollicoat SR 30D from BASF and Aquacoat ECD from FMC.

Example for Coating by Kollicoat SR 30D:
Tablet Formulation:

| | |
|---|---|
| Montelukast | 60 mg |
| Microcrystalline cellulose (MCC | 100 mg |
| Dibasic calcium phosphate dehydrate | 50 mg |
| Starch | 50 mg |
| Stearic acid | 2.6 mg |

Other commercial available excipients can also be used in the formulation.

Coating Formulation:

| | |
|---|---|
| Kollicoat SR 30D | 50 mg |
| Propylene glycol | 4 mg |
| Talc | 5 mg |
| Water | 41 mg |

Coating weight gain can be 3-10%.

Montelukast can be mixed with control release polymers at designed proportions and then granulated by commercial available binding excipients such as gum Arabic, starch. The granular of montelukast can then be compressed into tablets or encapsulated into hard capsules.

Bilayer Tablets

A tablet contains two layers, one layer designed for 20-30% of montelukast for immediately release within 30 min, another layer is for linear control release of rest of Montelukast for 10-12 hr.

Granules of Montelukast can also be in the different control release profile, such as 30% of the granules with 100% release within 1-2 hr, another 30% of granules release after 3-4 hr with 100% release within 3-4 hrs, and another 30% of granules release after 8 hrs.

Patches

Controlled release of montelukast may also be achieved through patches. For example, a transdermal patch, contains a montelukast depot layer that has a skin-facing side and a skin-distal side, and the depot layer contains a sufficient quantity of montelukast to maintain a useful flux of montelukast from the patch for a total time period of 12 hours or more. The patch also has an occlusive backing layer in contact with and covering the depot layer on the skin-distal side. The patch also has a rate-controlling means for controlling the diffusion of montelukast from the skin-facing side at a first flux of greater than zero but less than 2 mg/cm.sup.2 in any hour for a first time period of greater than zero but less than 5 hours, then at a second flux between 20 and 800 µg/cm.sup.2.h for a second time period of 7 hours or more. Other known patches are known in the art and may be modified to deliver montelukast in controlled release.

The foregoing is considered as illustrative only of the principles of the disclosure. Further, various modifications may be made of the disclosure without departing from the scope thereof.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Unless stated otherwise, it should not be assumed that multiple features, embodiments, solutions, or elements address the same or related problems or needs.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

The invention claimed is:

1. A method for improving cognitive function comprising:
selecting a patient, and
administering to the patient montelukast sodium in a solid dosage form, the solid dosage form comprising a therapeutically effective amount of montelukast sodium, wherein the amount of montelukast sodium is greater than about 20 mg, and
a rate release modifier, wherein the rate release modifier provides the patient a controlled release of montelukast sodium for at least about 4 hours.

2. A method for improving cognitive function comprising:
selecting a patient, and
administering to the patient a modified release solid dosage form of montelukast sodium having two portions, wherein a first portion comprises a first quantity of at least 5 mg of montelukast sodium in an immediate release formulation and, a second portion comprises a second quantity of at least 10 mg of montelukast sodium in a release-delaying matrix, wherein the total amount of montelukast sodium is at least about 20 mg.

3. The method of claim 2, wherein the first of multiple doses of a standard immediate release formulation having one fraction the amount of montelukast sodium is dosed about every two hours over a 12 hour period, and wherein said solid dosage form also provides therapeutically effective bioavailability for at least twelve hours after a single dose in a human patient.

4. The method of claim 2, wherein the total quantity of montelukast sodium in the modified release solid dosage form is from about 30 mg to about 90 mg.

5. The method of claim 2, wherein the total quantity of montelukast sodium in the immediate release formulation is from about 5 mg to about 25 mg.

6. The method of claim 2, wherein the total quantity of montelukast sodium in the release-delaying matrix is from about 10 mg to about 90 mg.

7. The method of claim 2, wherein the total quantity of montelukast sodium in the immediate release formulation is about 20 mg and wherein the total quantity of montelukast in the release-delaying matrix is about 60 mg.

8. The method of claim 2, additionally comprising folic acid or a reduced folate, and N-acetyl-L-cysteine.

9. A method for improving cognitive function comprising:
selecting a patient, and
administering to the patient a multi-particulate pharmaceutical solid dosage form of a montelukast sodium providing a modified release profile comprising a population of immediate release beads comprising montelukast sodium,
a population of extended release beads, wherein said extended release beads comprise a montelukast sodium core particle and an extended release coating, wherein the multi-particulate pharmaceutical dosage form of a montelukast sodium comprises at least about 20 mg of montelukast sodium in combined immediate release beads and extended release beads.

10. The method of claim 9,
wherein said solid dosage form when dissolution tested using United States Pharmacopoeia Apparatus 2 (paddles@50 rpm) in 900 mL of 0.1N HCl at 37° C. exhibits a drug release profile substantially corresponding to the following pattern:
after about 2 hours, no more than about 40% of the total active is released;
after about 4 hours, from about 40-65% of the total active is released
after about 8 hours, from about 60-85% of the total active is released;
wherein said solid dosage form provides therapeutically effective plasma concentration over a period of 12 hours to improve cognitive function when administered to a patient in need thereof.

11. The method of claim 9, wherein the multi-particulate pharmaceutical solid dosage form additionally comprises at least one nutrient selected from vitamin $B_{12}$, vitamin $B_6$, an omega-3 fatty acid, or vitamin $B_2$.

12. The method of claim 1, wherein the controlled release provides the patient a therapeutic amount of montelukast sodium for improving cognitive function over the course of a day.

13. The method of claim 1, wherein the cognitive function is memory.

14. The method of claim 1, wherein the a solid dosage form is a tablet or a capsule.

15. The method of claim 2, wherein the a modified release solid dosage form is a capsule or tablet.

16. The method of claim 1, wherein the cognitive function is memory, mental clarity, mood, or attention span.

17. The method of claim 2, wherein the cognitive function is memory, mental clarity, mood, or attention span.

18. The method of claim 10, wherein the cognitive function is memory, mental clarity, mood, or attention span.

* * * * *